United States Patent [19]

Moser

[11] 4,369,142

[45] Jan. 18, 1983

[54] PROCESS FOR PRODUCING N-PHOSPHONOMETHYLGLYCINE

[75] Inventor: Hans Moser, Magden, Switzerland

[73] Assignee: Ciba-Geigy Corporation, Ardsley, N.Y.

[21] Appl. No.: 327,138

[22] Filed: Dec. 3, 1981

[51] Int. Cl.³ .............................................. C07F 9/38
[52] U.S. Cl. ............................................ 260/502.5 F
[58] Field of Search ................................. 260/502.5 F

[56] References Cited

U.S. PATENT DOCUMENTS

| | | | |
|---|---|---|---|
| 3,799,758 | 3/1974 | Franz | 260/502.5 |
| 3,956,370 | 5/1976 | Parry | 260/502.5 |
| 4,094,928 | 6/1978 | Gaertner | 260/502.5 |
| 4,237,065 | 12/1980 | Ehrst | 260/502.5 |

*Primary Examiner*—Joseph E. Evans
*Attorney, Agent, or Firm*—Karl F. Jorda

[57] ABSTRACT

The novel process for producing N-phosphonomethylglycine comprises reacting aminomethanephosphonic acid with glyoxal, in an aqueous medium, in the presence of sulfur dioxide. The active substance obtained is a herbicide having a very wide spectrum of activity.

11 Claims, No Drawings

PROCESS FOR PRODUCING N-PHOSPHONOMETHYLGLYCINE

The present invention relates to a novel process for producing N-phosphonomethylglycine of the formula I

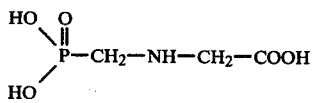
(I)

by reaction of aminomethanephosphonic acid with glyoxal in an aqueous medium in the presence of sulfur dioxide.

N-Phosphonomethylglycine is a herbicide which has a very wide spectrum and which has little or no residual effects. The production and use thereof are described in the U.S. Pat. No. 3,799,758.

It is known that on reaction of glycine, formaldehyde and phosphorous acid in the molar ratio of 1:1:1, there is formed, instead of the desired N-phosphonomethylglycine mainly N,N-bis-phosphonomethylglycine (cp. U.S. Pat. No. 3,956,370). This product can then be converted electrolytically (U.S. Pat. No. 3,835,000) into phosphonomethylglycine.

In order to overcome the difficulties associated with the aforementioned process, it has been suggested that N-phosphonomethylglycine be produced by a process comprising firstly reacting an N-substituted glycine with formaldehyde and phosphorous acid to the corresponding N-substituted N-phosphonomethylglycine, and subsequently detaching from this the substituent originally present on the nitrogen atom. There is thus described for example in the U.S. Pat. No. 3,956,370 the production of N-phosphonomethylglycine by reaction of N-benzylethyl-glycinate with formaldehyde and phosphorous acid with simultaneous hydrolysis of the ester group to give N-benzyl-N-phosphonomethylglycine and subsequent removal of the benzyl group, as benzyl bromide, with strong hydrobromic acid. N-Phosphonomethylglycine is obtained in this manner in a yield of about 40%. This process is not advantageous for commercially producing N-phosphonomethylglycine on account of the low yield and in view of the lacrimatoric action of the benzyl bromide formed as a by-product.

It is therefore the object of the present invention to provide a process by which N-phosphonomethylglycine can be produced in good yield and with the formation of by-products which are easy to handle and environmentally favourable.

It is suggested according to the invention to produce N-phosphonomethylglycine by reacting aminomethanephosphonic acid of the formula II

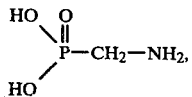
(II)

in an aqueous medium, with glyoxal of the formula II

OHC—CHO (III)

in the presence of sulfur dioxide, and isolating the resulting product.

An advantageous procedure for the reaction is to suspend the aminomethanephosphonic acid and glyoxal in water, and to subsequently introduce sulfur dioxide into the suspension.

The introduction of the sulfur dioxide gas can be performed with or without cooling of the reaction solution. The reaction mixture is however advantageously cooled to 0°-30° C., particularly to 5°-20° C., during the time the sulfur dioxide gas is being introduced. The amount of sulfur dioxide gas introduced is so regulated that the amount is between that required to clarify the suspension and that sufficing to saturate the mixture. A saturation of the reaction solution with sulfur dioxide is however an advantage.

After completion of the introduction of the sulfur dioxide required, the solution is heated to a temperature of between 60° and 120° C. A temperature of between 85° C. and the boiling temperature of the reaction mixture is advantageous. The reaction solution is heated for a period of 5-120 minutes. Reaction times of 15-60 minutes, and in particular of 20-40 minutes, are advantageous. The sulfur dioxide gas introduced is again liberated during heating and can be recovered.

The employed glyoxal can be used, in the reaction according to the invention, both as an aqueous solution of the monomer and as polymer.

In order to obtain a high yield, it is of advantage to keep the amount of water as small as possible, since the reaction product is soluble in water. The further addition of water as solvent can be dispensed with in particular when dilute aqueous solutions of glyoxal are being used.

In the reaction according to the invention, the sulfur dioxide can also be in the bound form instead of being in the form of sulfur dioxide gas. Especially suitable in this respect are alkali metal salts and alkaline-earth metal salts of sulfurous acid, particularly hydrogen sulfite of sodium, potassium or calcium.

Also adducts of glyoxal and sulfurous acid, and salts thereof, can be used as starting products for the reaction according to the invention. Suitable in a particular manner for this purpose is the commercially obtainable glyoxal-bis-(sodium hydrogen sulfite) hydrate.

The substitution of sulfur dioxide by salts thereof or by reaction products of these with glyoxal is advantageous with respect to carrying out the process of the invention in the laboratory by virtue of the greater ease of operation; however, also in the case of applying the process on a commercial scale, the use of sulfur dioxide gas is of advantage for reasons of cost, in particular because the sulfur dioxide released again during the reaction can be recovered and re-utilised in the reaction of the following reaction batch.

An advantageous embodiment of the process according to the invention comprises saturating at 5°-20° C. the suspension of aminomethanephosphonic acid and glyoxal in water with sulfur dioxide, heating the formed solution at 85°-105° C. for 20-40 minutes, and isolating the product by crystallisation.

The reactants, aminomethanephosphonic acid and glyoxal, are as a rule reacted in equimolar amounts.

The Examples which follow serve to further illustrate the present invention.

EXAMPLE 1

Sulfur dioxide gas is introduced at 10°-15° C., with vigorous stirring and with cooling, into a suspension of 11.1 g (0.1 mol) of aminomethanephosphonic acid and 11.4 ml (0.1 mol) of 40% aqueous glyoxal in 40 ml of water until a clear solution has formed. After further stirring at room temperature for half an hour, the solution is refluxed for half an hour, in the course of which an intense evolution of sulfur dioxide occurs, and the solution turns dark brown. The reaction mixture is afterwards cooled to 5° C.; the formed precipitate is separated, washed with a small amount of ice-water and recrystallised from water. The yield is 8.1 g (48%) of pure N-phosphonomethylglycine; decomposition: 236° C.

EXAMPLE 2

A suspension of 11.1 g (0.1 mol) of aminomethanephosphonic acid and 7.2 g (0.1 mol) of 80% polymeric glyoxal in 40 ml of water is treated with sulfur dioxide and further processed in the manner described in Example 1; yield: 7.7 g (45.5%) of N-phosphonomethylglycine; decomposition: 244° C.

EXAMPLE 3

Sulfur dioxide gas is introduced, without cooling and with vigorous stirring, into a suspension of 11.1 g (0.1 mol) of aminomethanephosphonic acid and 7.2 g (0.1 mol) of 80% polymeric glyoxal in 40 ml of water until saturation is attained, in the course of which the solution turns yellowish-orange and the temperature rises to 42° C. The solution is subsequently stirred and refluxed, during which time the colour of the solution becomes dark brown. The solution is filtered hot and then cooled to 5° C.; the precipitate is afterwards separated, washed with a small amount of ice-cold water and dried. The resulting yield is 10.6 g (62.8%) of N-phosphonomethylglycine; decomposition: 235° C.

EXAMPLE 4

A suspension of 15.6 g (0.055 mol) of glyoxal-bis-(sodium hydrogen sulfite) hydrate and 5.5 g (0.05 mol) of aminomethanephosphonic acid in 30 ml of water is refluxed with stirring. The evolution of sulfur dioxide commences when the temperature reaches 85° C.; a clear solution is formed and is refluxed for 40 minutes. After cooling of the reaction mixture to room temperature, 11 ml (0.11 mol) of 32% hydrochloric acid are added, and the mixture is concentrated by evaporation. The oily residue is triturated with 40 ml of 36% hydrochloric acid; the salt which has precipitated is then separated, and the solution is again concentrated by evaporation. The oil obtained is crystallised by the addition of 150 ml of ethanol. This suspension is neutralised to Congo red by propylene oxide being added; the precipitate is separated, washed with ethanol and dried.

Recrystallisation from water yields 4.5 g (53.2%) of N-phosphonomethylglycine; decomposition: 228° C.

What is claimed is:

1. A process for producing N-phosphonomethylglycine of the formula I

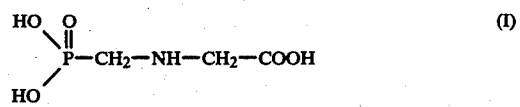

by reacting aminomethanephosphonic acid of the formula II

in an aqueous medium, with glyoxal of the formula III

in the presence of sulfur dioxide, and isolating the resulting product.

2. A process according to claim 1, wherein the sulfur dioxide is introduced into a suspension of aminomethanephosphonic acid and glyoxal in water.

3. A process according to either of claims 1 or 2, wherein the minimum amount of sulfur dioxide is such that a clear solution is formed.

4. A process according to claim 3, wherein the reaction mixture is saturated with sulfur dioxide.

5. A process according to claim 1, wherein the reaction mixture is heated to 60°-120° C.

6. A process according to claim 5, wherein the temperature is between 85° C. and boiling temperature of the reaction mixture.

7. A process according to claim 1, wherein an aqueous solution of monomeric or polymeric glyoxal is used.

8. A process according to claim 5, wherein the solution is heated for 5-120 minutes.

9. A process according to claim 1, wherein the sulfur dioxide is used in the bound form.

10. A process according to claim 9, wherein the sulfur dioxide is used in the form of hydrogen sulfite of sodium, potassium or calcium, or, together with glyoxal, in the form of its bis hydrogen sulfite with sodium, potassium or calcium.

11. A process according to claim 1, wherein a suspension of aminomethanephosphonic acid and glyoxal in water is saturated at 5°-20° C. with sulfur dioxide, the formed solution is heated at 85°-105° C. for 20-40 minutes, and the product is isolated by crystallisation.

* * * * *